United States Patent
Ajiki et al.

(10) Patent No.: US 9,393,410 B2
(45) Date of Patent: Jul. 19, 2016

(54) POSTURE CORRECTION APPARATUS AND POSTURE CORRECTION METHOD

(71) Applicant: Panasonic Intellectual Property Management Co., Ltd., Osaka (JP)

(72) Inventors: Kaori Ajiki, Osaka (JP); Toshimitsu Minowa, Kanagawa (JP); Sachiko Takeshita, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/558,682

(22) Filed: Dec. 2, 2014

(65) Prior Publication Data

US 2015/0182747 A1 Jul. 2, 2015

(30) Foreign Application Priority Data

Dec. 27, 2013 (JP) ................. 2013-272301

(51) Int. Cl.
*A61N 1/36* (2006.01)
*A61N 1/04* (2006.01)
*A61N 1/372* (2006.01)

(52) U.S. Cl.
CPC .......... *A61N 1/36003* (2013.01); *A61N 1/0452* (2013.01); *A61N 1/0476* (2013.01); *A61N 1/0484* (2013.01); *A61N 1/37264* (2013.01)

(58) Field of Classification Search
CPC ...... A61B 5/0488; A61B 5/4519; A61B 5/11; A61B 5/0008; A61B 5/1116; A61B 5/112; A61B 5/1124; A61B 5/0484; A61B 5/01; A61B 5/04004; A61B 5/04012; A61B 5/1114; A61B 5/224; A61B 5/441; A61B 5/486; A61B 5/72; G06F 19/3418; G06F 3/015; G06F 19/3437; A61N 1/36014; A61N 1/0553; A61N 1/36139; A61N 1/36146; A61N 1/36535; A61N 1/36542; A61N 1/0452; A61N 1/0476; A61N 1/36003; G08B 21/0453; G06Q 50/22

See application file for complete search history.

(56) References Cited

U.S. PATENT DOCUMENTS

| | | | |
|---|---|---|---|
| 2007/0250119 A1* | 10/2007 | Tyler | ................. A61N 1/36014 607/2 |
| 2008/0097530 A1 | 4/2008 | Muccio et al. | |
| 2009/0224231 A1 | 9/2009 | Takeuchi et al. | |
| 2010/0305484 A1 | 12/2010 | Grollier et al. | |

(Continued)

FOREIGN PATENT DOCUMENTS

| | | |
|---|---|---|
| CA | 2 877 041 | 1/2014 |
| CN | 103446669 | 12/2013 |
| DE | 10 2011 014 624 | 9/2012 |

(Continued)

OTHER PUBLICATIONS

European Search Report mailed May 11, 2015 in European Patent Application No. 14196205.0.

*Primary Examiner* — Deborah Malamud

(74) *Attorney, Agent, or Firm* — Greenblum & Bernstein P.L.C.

(57) ABSTRACT

A posture correction apparatus includes an obtaining unit configured to obtain information related to a muscle condition in a body, a determination unit configured to determine muscle stimulation to be provided to the body, based on the obtained information, and a stimulation unit configured to provide the determined muscle stimulation to the body.

3 Claims, 17 Drawing Sheets

(56) References Cited

U.S. PATENT DOCUMENTS

2011/0295083 A1* 12/2011 Doelling ............... A61B 5/103 600/301
2015/0057734 A1    2/2015  Mushahwar et al.

FOREIGN PATENT DOCUMENTS

| | | |
|---|---|---|
| DE | 20 2012 102 393 U | 11/2013 |
| JP | 4-312472 | 11/1992 |
| JP | 2002-238930 | 8/2002 |
| JP | 2007-178256 | 7/2007 |
| JP | 2011-505897 | 3/2011 |
| JP | 2013-168575 | 8/2013 |
| WO | 2006/046521 | 5/2006 |
| WO | 2013/113099 | 8/2013 |
| WO | 2013/188650 | 12/2013 |

* cited by examiner

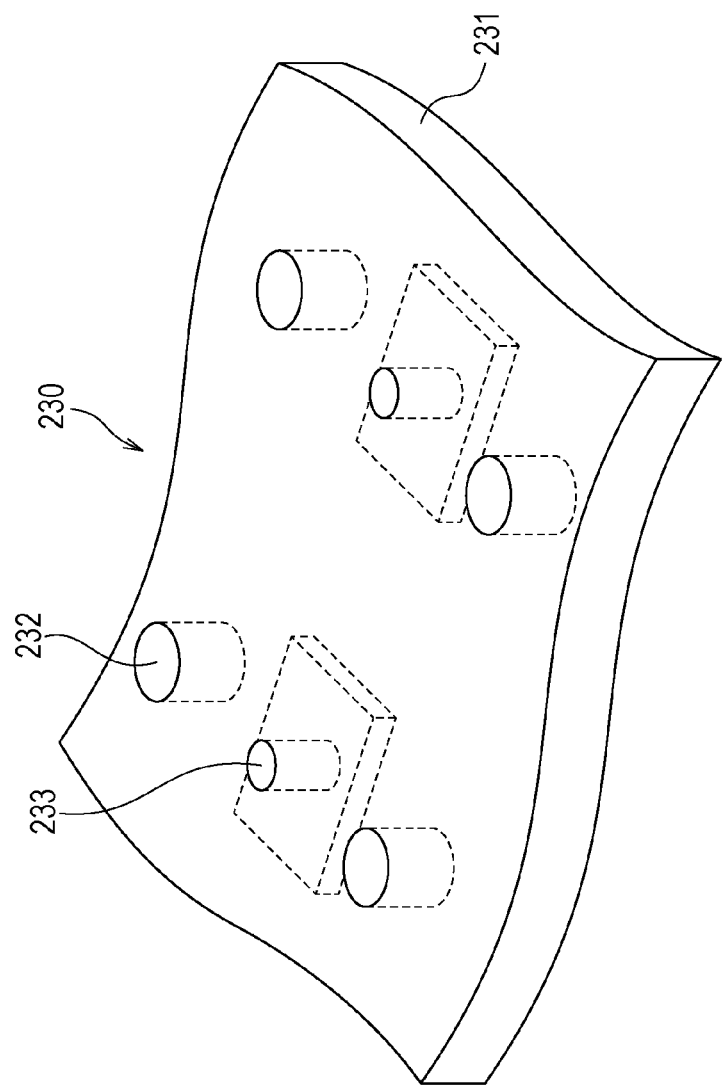

| MUSCLE | MUSCLE CONDITION | | | |
|---|---|---|---|---|
| | FIRST SUBJECT | SECOND SUBJECT | .... | L-TH SUBJECT |
| LATISSIMUS DORSI | 0 | 1 | .... | 1 |
| TERES MAJOR | 1 | 1 | .... | 0 |
| TERES MINOR | 1 | 1 | .... | 0 |
| SUPRASPINATUS | 1 | 1 | .... | 1 |
| INFRASPINATUS | 1 | 1 | .... | 1 |
| TRAPEZIUS (UPPER) | 1 | 1 | .... | 1 |
| TRAPEZIUS (MIDDLE) | 1 | 1 | .... | 1 |
| TRAPEZIUS (LOWER) | 0 | 1 | .... | 1 |
| TRAPEZIUS (LOWER) | 0 | 1 | .... | 1 |
| ⋮ | ⋮ | ⋮ | ⋮ | ⋮ |

| MUSCLE | EMS ELECTRODE PAIR |
|---|---|
| LATISSIMUS DORSI | 1ST TO 4TH EMS ELECTRODE PAIRS |
| TERES MAJOR | 5TH AND 6TH EMS ELECTRODE PAIRS |
| TERES MINOR | 7TH AND 8TH EMS ELECTRODE PAIRS |
| SUPRASPINATUS | 9TH AND 10TH EMS ELECTRODE PAIRS |
| INFRASPINATUS | 11TH AND 12TH EMS ELECTRODE PAIRS |
| TRAPEZIUS (UPPER) | 13TH AND 14TH EMS ELECTRODE PAIRS |
| TRAPEZIUS (MIDDLE) | 15TH AND 16TH EMS ELECTRODE PAIRS |
| TRAPEZIUS (LOWER) | 17TH AND 18TH EMS ELECTRODE PAIRS |
| TRAPEZIUS (LOWER) | 19TH AND 20TH EMS ELECTRODE PAIRS |
| ⋮ | ⋮ |
| ⋯ | ⋯ N-TH EMS ELECTRODE PAIRS |

| MUSCLE | NECESSITY OF OPERATION OF EMS ELECTRODE PAIR | | | |
| --- | --- | --- | --- | --- |
| | FIRST SUBJECT | SECOND SUBJECT | .... | L-TH SUBJECT |
| FIRST EMS ELECTRODE PAIR | 0 | 1 | .... | 1 |
| SECOND EMS ELECTRODE PAIR | 0 | 1 | .... | 1 |
| ⋮ | ⋮ | ⋮ | ⋮ | ⋮ |
| N-TH EMS ELECTRODE PAIR | 1 | 1 | .... | 0 |

| PRESSURE SENSOR | DETECTED VALUE OF PRESSURE SENSOR | | | |
| --- | --- | --- | --- | --- |
| | FIRST SUBJECT | SECOND SUBJECT | .... | L-TH SUBJECT |
| FIRST PRESSURE SENSOR | $PD1_1$ | $PD1_2$ | .... | $PD1_L$ |
| SECOND PRESSURE SENSOR | $PD2_1$ | $PD2_2$ | .... | $PD2_L$ |
| ⋮ | ⋮ | ⋮ | ⋮ | ⋮ |
| M-TH PRESSURE SENSOR | $PDM_1$ | $PDM_2$ | .... | $PDM_L$ |

FIG. 12

| MUSCLE | FIRST PRESSURE SENSOR | SECOND PRESSURE SENSOR | $\cdots$ | M-TH PRESSURE SENSOR |
|---|---|---|---|---|
| FIRST EMS ELECTRODE PAIR | $a_{11}$ | $a_{12}$ | $\cdots$ | $a_{1M}$ |
| SECOND EMS ELECTRODE PAIR | $a_{21}$ | $a_{22}$ | $\cdots$ | $a_{2M}$ |
| $\vdots$ | $\vdots$ | $\vdots$ | $\vdots$ | $\vdots$ |
| N-TH EMS ELECTRODE PAIR | $a_{N1}$ | $a_{N2}$ | $\cdots$ | $a_{NM}$ |

350

POSTURE CORRECTION APPARATUS AND POSTURE CORRECTION METHOD

CROSS REFERENCE TO RELATED APPLICATION

The present application claims the benefit of Japanese Patent Application No. 2013-272301 filed on Dec. 27, 2013. The entire disclosure of the above-identified application, including the specification, drawings and claims, is incorporated herein by reference in its entirety.

BACKGROUND

1. Technical Field

The present disclosure relates to a posture correction apparatus and a posture correction method.

2. Description of the Related Art

A posture correction supporter (see, for example, Japanese Unexamined Patent Application Publication No. 2002-238930), which is a medical health product, has a function to maintain a human body in a predetermined posture by being attached to a predetermined position on the body. The posture correction supporter has the capability of changing the posture of the body from a poor posture, such as a rounded back posture, to a good posture, such as a straight back posture, and maintaining the body in good posture.

However, once the posture correction supporter is removed from the body, the body is likely to return to the former poor posture over time. In addition, the posture correction supporter is not necessarily wearable all the time. It is thus desirable to maintain the body in good posture by using its own muscle strength.

In addition, the capability to maintain the body in good posture by using its own muscle strength is advantageous for improving aesthetic appearance including facial impression as well as for improving health.

For example, the trapezius muscle, which is one of the back muscles, connects to the frontalis muscle, which is one of the facial muscles, via the galea aponeurotia in the head and the occipitalis muscle. Thus, increasing the strength of the trapezius muscle may promote an increase in the strength of the frontalis muscle, lift up the facial skin, and reduce the occurrence of facial issues which may be caused by sagging skin, such as nasolabial folds. That is, exercising necessary muscles may make it possible to reduce the sagging of facial skin which may be caused by a reduction in the strength of the muscles in the face and body (hereinafter referred to simply as "facial sagging").

One of the possible solutions to address the issues described above is to exercise muscles by using a device for providing external stimulation to the muscles (see, for example, Japanese Unexamined Patent Application Publication No. 4-312472), such as by using electrical muscle stimulation (EMS) electrodes, to reduce facial sagging.

SUMMARY

However, it is difficult to accurately determine which muscles to exercise and how much exercise to do in order to maintain a predetermined posture which leads to reduction in facial sagging. In the related art, therefore, facial sagging is difficult to reduce.

One non-limiting and exemplary embodiment provides a posture correction apparatus which may reduce facial sagging.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a posture correction apparatus that includes an obtaining unit configured to obtain information related to a muscle condition in a body, a determination unit configured to determine muscle stimulation to be provided to the body, based on the obtained information, and a stimulation unit configured to provide the determined muscle stimulation to the body.

Note that general and specific aspects of the present disclosure may be implemented in a form of a method.

A posture correction apparatus according to an aspect of the present disclosure may reduce facial sagging.

BRIEF DESCRIPTION OF THE DRAWINGS

FIG. 4 is a diagram illustrating an example arrangement of the sheet device in the second embodiment.

FIG. 8 is a diagram illustrating an example of learning-specific muscle-condition data in the second embodiment.

FIG. 9 is a diagram illustrating an example of a muscle-to-electrode correspondence in the second embodiment.

FIG. 10 is a diagram illustrating an example of a learning-specific operation necessity matrix in the second embodiment.

FIG. 11 is a diagram illustrating an example of a learning-specific pressure value matrix in the second embodiment.

FIG. 12 is a diagram illustrating an example of a coefficient matrix in the second embodiment.

DETAILED DESCRIPTION

Embodiments of the present disclosure will be described in detail hereinafter with reference to the drawings.

First Embodiment

A first embodiment of the present disclosure is an example of a basic embodiment of the present disclosure.

Figure 1:
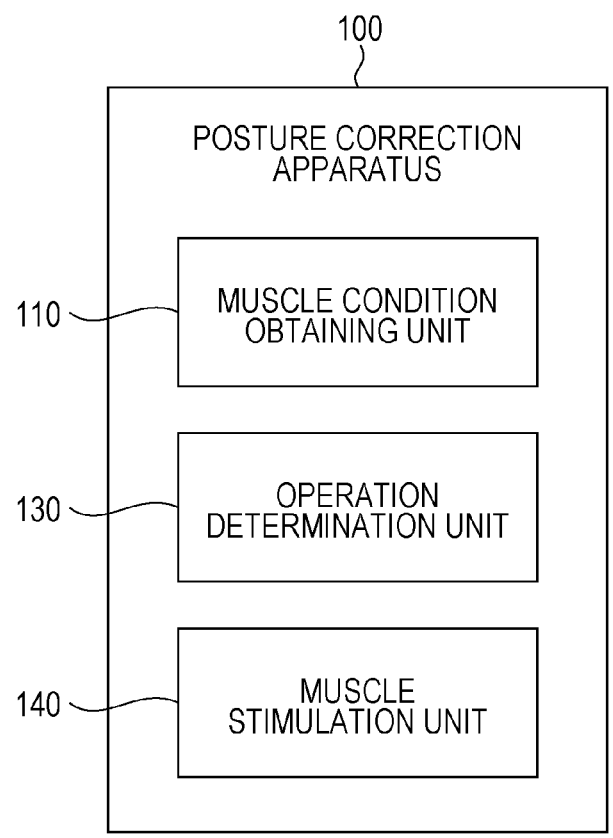
FIG. 1 is a diagram illustrating an example configuration of a posture correction apparatus according to a first embodiment of the present disclosure.

FIG. 1 is a diagram illustrating an example configuration of a posture correction apparatus according to this embodiment.

In FIG. 1, a posture correction apparatus 100 is an apparatus configured to maintain a human body in a predetermined posture which leads to reduction in facial sagging by being attached to a predetermined position on the body. The posture correction apparatus 100 includes a muscle condition obtaining unit 110, an operation determination unit 130, and a muscle stimulation unit 140.

The muscle condition obtaining unit 110 obtains information related to a muscle condition in the body while the posture correction apparatus 100 is attached to a predetermined position on the body. The muscle condition obtaining unit 110 may obtain the muscle condition through the skin of the body while the posture correction apparatus 100 is in contact with the skin.

The operation determination unit 130 determines muscle stimulation to be provided to the body to promote the body to be maintained in a predetermined posture by the body itself, based on the obtained condition of the muscles.

The muscle stimulation unit 140 provides the determined muscle stimulation to the body. The muscle stimulation unit 140 may provide muscle stimulation to the body through the skin of the body while the posture correction apparatus 100 is in contact with the skin.

The posture correction apparatus 100 includes, for example, a central processing unit (CPU) and a storage medium that stores a control program, such as a read only memory (ROM), and a working memory such as a random access memory (RAM) although these elements are not illustrated in the drawing. In this case, the CPU executes the control program, making feasible the functions of the components described above.

The posture correction apparatus 100 having the configuration described above may provide muscle training so that the body can be maintained in a predetermined posture which leads to reduction in facial sagging by using its own muscle strength. That is, the posture correction apparatus 100 may reduce facial sagging.

Second Embodiment

A second embodiment of the present disclosure is an example of a specific embodiment of the present disclosure, which is applied to a posture correction supporter configured to correct back posture.

External Appearance and Configuration of Posture Correction Apparatus

First, a description will be given of the external appearance and configuration of a posture correction apparatus according to this embodiment.

External Appearance of Posture Correction Apparatus

Figure 2A:
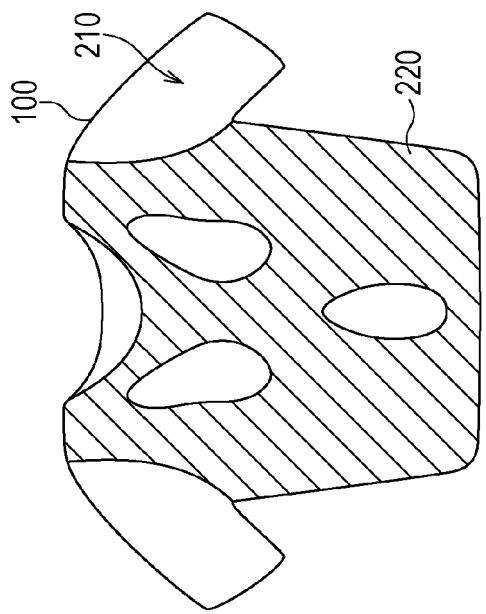
FIGS. 2A and 2B are diagrams illustrating an example external appearance of a posture correction apparatus according to a second embodiment of the present disclosure.
Figure 2B:
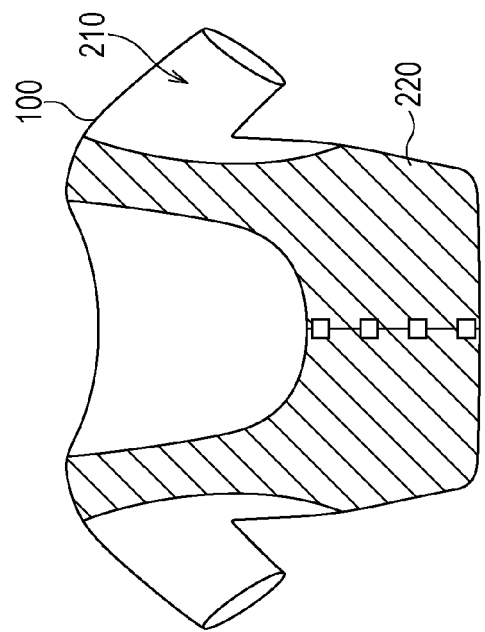

FIGS. 2A and 2B are diagrams illustrating an example external appearance of a posture correction apparatus 10 according to this embodiment. FIG. 2A illustrates the external appearance of the posture correction apparatus 10 when viewed from the front. FIG. 2B illustrates the external appearance of the posture correction apparatus 10 when viewed from the back.

As illustrated in FIGS. 2A and 2B, the posture correction apparatus 100 has a shape that covers the chest, back, and shoulders of the body, and is worn as, for example, underwear on the upper part of the body. The posture correction apparatus 100 includes an elastic portion 210 and an inelastic portion 220, both of which may be fabric members. While the posture correction apparatus 100 is worn on the upper part of the body, due to the three-dimensional shape and inelasticity, the inelastic portion 220 (hatched portions in FIGS. 2A and 2B) has a function to maintain the body in a good, straight back posture which leads to reduction in facial sagging. In the following, this posture is referred to as the "ideal posture".

For a person who is able to achieve a posture that is close to the ideal posture by using their own muscle strength, the repulsion force acting on the body of the person from the inelastic portion 220 is low. Accordingly, the pressure between the inelastic portion 220 and the skin (hereinafter referred to as the "skin pressure") is low as a whole.

In contrast, for a person who is not able to achieve a posture that is close to the ideal posture by using their own muscle strength, the repulsion force acting on the body from the inelastic portion 220 is high. Accordingly, there exists a portion with high skin pressure. The portion with high skin pressure corresponds to the position of weak muscles.

Accordingly, while worn on the upper part of the body, the posture correction apparatus 100 obtains skin pressure as information indicating a muscle condition. Then, the posture correction apparatus 100 stimulates the muscles to be exercised to maintain the body in the ideal posture by using its own muscle strength, based on the obtained skin pressure.

The posture correction apparatus 100 obtains skin pressure and provides muscle stimulation by using a sheet device disposed on the inner side of the inelastic portion 220.

Arrangement of Sheet Device

Figure 3A:
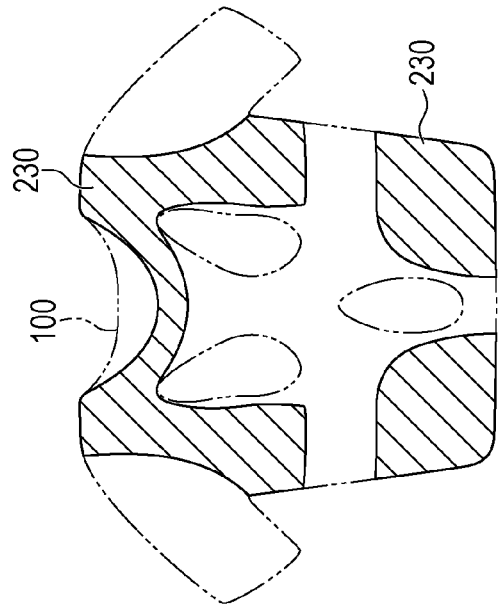
FIGS. 3A and 3B are diagrams illustrating an example arrangement of a sheet device in the posture correction apparatus according to the second embodiment.
Figure 3B:
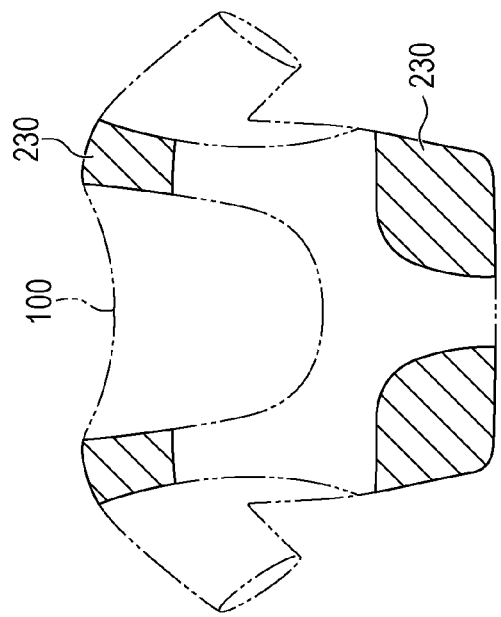

FIGS. 3A and 3B are diagrams illustrating an example arrangement of a sheet device in the posture correction apparatus 100. FIG. 3A corresponds to FIG. 2A, and FIG. 3B corresponds to FIG. 2B.

As illustrated in FIGS. 3A and 3B, for example, a sheet device 230 (hatched portions in FIGS. 3A and 3B) is arranged in a region in contact with the shoulders and the skin outside the shoulder blades, a region in contact with the skin of the left flank, and a region in contact with the skin of the right flank. The above regions correspond to the trapezius muscle, the latissimus dorsi muscle, the teres major muscle, the teres minor muscle, the supraspinatus muscle, the infraspinatus muscle, and so forth.

The sheet device 230 has a configuration in which a plurality of pressure sensors and a plurality of EMS electrode pairs are arranged on a sheet member. The sheet member has a thickness of, for example, 0.1 mm to 1 mm.

Configuration of Sheet Device

FIG. 4 is a diagram illustrating an example configuration of the sheet device 230. In FIG. 4, only a representative portion of the entire sheet device 230 is illustrated.

In FIG. 4, the sheet device 230 has a configuration in which pressure sensors 232 and EMS electrodes 233 are buried in a sheet member 231.

The sheet member 231 is an elastic base member. Examples of the sheet member 231 may include the sheet member described in Japanese Unexamined Patent Application Publication (Translation of PCT Application) No. 2011-505897.

Each of the pressure sensors 232 detects a pressure applied normal to a pressure detection surface of the pressure sensor 232, and outputs a detection result. Examples of the pressure sensors 232 include the pressure sensors that include organic thin film transistors, described in Japanese Patent No. 5197960 and Japanese Unexamined Patent Application Publication No. 2007-178256. Examples of the pressure sensors 232 may also include a pressure sensor that includes the flexible sheet-shaped organic thin film transistor described in Japanese Unexamined Patent Application Publication No. 2013-168575. In the organic thin film transistor described in Japanese Unexamined Patent Application Publication No. 2013-168575, a conductor that makes a connection between a circuit substrate and a transistor element is formed of a base member with elasticity.

Each of the EMS electrodes 233 causes a weak current to flow to a muscle located between a plus (or positive) electrode surface of the EMS electrode 233 and a minus (or negative) electrode surface of the EMS electrode 233 to contract the muscle ("muscle stimulation"). Examples of the EMS electrodes 233 include the EMS electrodes described in Japanese Unexamined Patent Application Publication No. 4-312472.

The pressure detection surfaces of the pressure sensors 232, and the electrode surfaces of the EMS electrodes 233 are exposed on the surface of the sheet member 231 that comes into contact with the skin. That is, each of the pressure sensors 232 and each of the EMS electrodes 233 come into contact with the skin while the posture correction apparatus 100 is worn on the body, and obtain skin pressure through the skin and provide muscle stimulation through the skin.

Configuration of Pressure Sensor

Figure 5:
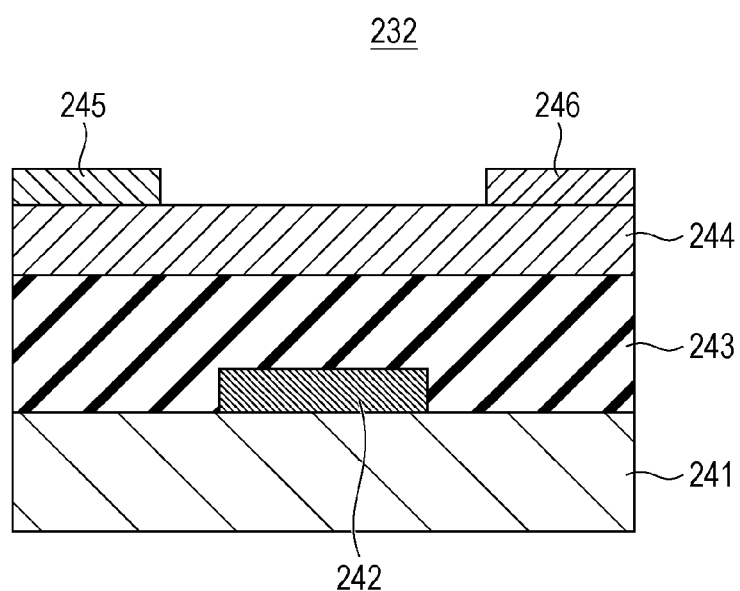
FIG. 5 is a schematic diagram illustrating an example structure of a pressure sensor in the second embodiment.

FIG. 5 is a schematic diagram illustrating an example structure of each of the pressure sensors 232 in a case where the pressure sensor 232 includes an organic thin film transistor.

The pressure sensor 232 has a configuration in which a gate insulating layer 243 and an organic molecular layer 244 are stacked on a gate electrode layer 242 disposed on a surface of an elastic base member 241. The pressure sensor 232 further has a configuration in which a source electrode 245 and a drain electrode 246 are disposed on a surface of the organic molecular layer 244 so as to be away from each other.

The gate insulating layer 243 is made of flexible material such as natural rubber, polyisoprene rubber, styrene-butadiene copolymer rubber, polybutadiene rubber, or butyl rubber. The electric capacitance between the gate, source, and drain changes depending on the degree of compression of the gate insulating layer 243. By detecting the electric capacitance, it is possible to detect the pressure applied to the pressure sensor 232.

In this embodiment, by way of example, the sheet device 230 has M pressure sensors 232 arranged thereon. Part of the sheet member 231 may form the elastic base member 241 of the corresponding pressure sensor 232.

Arrangement of EMS Electrodes

Figure 6A:
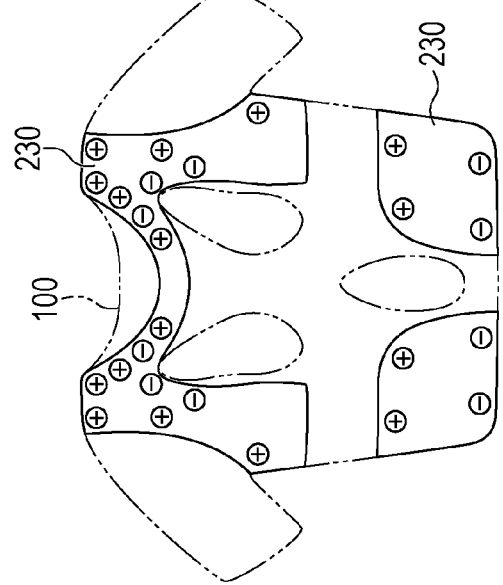
FIGS. 6A and 6B are diagrams illustrating an example arrangement of EMS electrodes in the second embodiment.
Figure 6B:
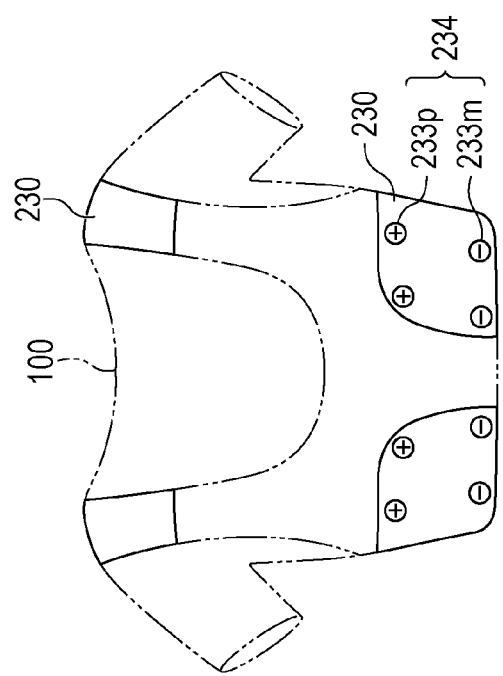

FIGS. 6A and 6B are diagrams illustrating an example arrangement of EMS electrodes. FIG. 6A corresponds to FIG. 3A, and FIG. 6B corresponds to FIG. 3B.

In FIGS. 6A and 6B, the sheet device 230 has arranged thereon a plurality of EMS electrode pairs 234 each composed of a plus (or positive) EMS electrode $233_p$ and a minus (or negative) EMS electrode $233_m$.

Each of the EMS electrode pairs 234 is arranged so as to stimulate any of the muscles necessary to maintain the ideal posture. Examples of the muscles necessary to maintain the ideal posture include the trapezius muscle, the latissimus dorsi muscle, the teres major muscle, the teres minor muscle, the supraspinatus muscle, and the infraspinatus muscle.

In this embodiment, by way of example, the sheet device 230 has N EMS electrode pairs 234.

Functional Configuration of Posture Correction Apparatus

Figure 7:
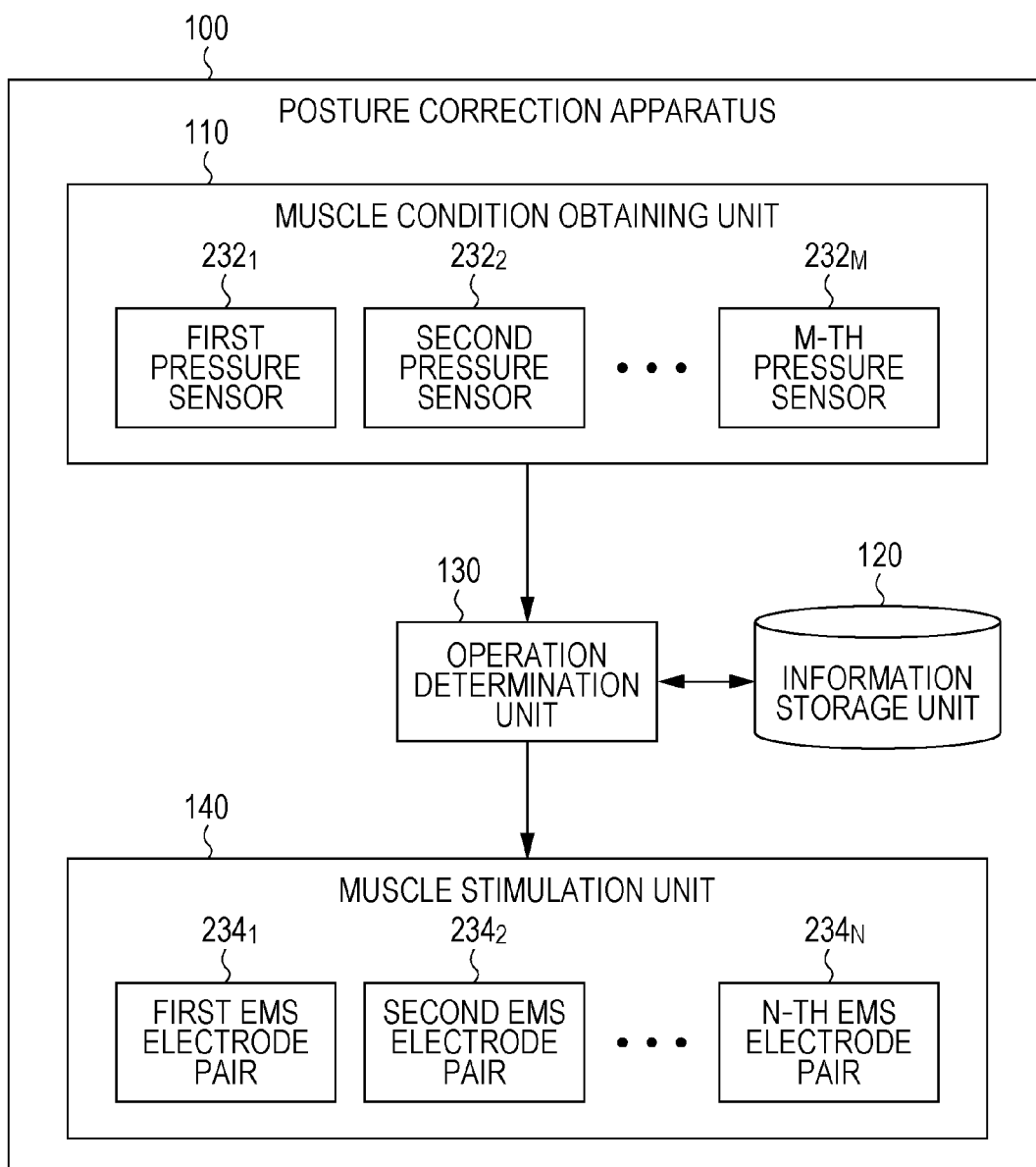
FIG. 7 is a diagram illustrating an example functional configuration of the posture correction apparatus according to the second embodiment.

FIG. 7 is a diagram illustrating an example functional configuration of the posture correction apparatus 100.

The posture correction apparatus 100 includes a muscle condition obtaining unit 110, an information storage unit 120, an operation determination unit 130, and a muscle stimulation unit 140. The muscle condition obtaining unit 110 includes the first to M-th pressure sensors $232_1$ to $232_M$ described with reference to FIGS. 3A and 3B and FIGS. 4 and 5. The muscle stimulation unit 140 includes the first to N-th EMS electrode pairs $234_1$ to $234_N$ described with reference to FIGS. 3A and 3B, FIG. 4, and FIGS. 6A and 6B.

The information storage unit 120 and the operation determination unit 130 are provided in, for example, a control unit (not illustrated) disposed outside the inelastic portion 220 in the center of the chest. The control unit includes, for example, a CPU, a storage medium that stores a control program, such as a ROM, and a working memory such as a RAM. In this case, the CPU executes the control program, making feasible the functions of the information storage unit 120 and the operation determination unit 130.

Each of the first to M-th pressure sensors $232_1$ to $232_M$ and the first to N-th EMS electrode pairs $234_1$ to $234_N$ is connected to the operation determination unit 130 via a cable (not illustrated). That is, the operation determination unit 130 is configured to output a control signal to each pressure sensor and receive, as input, a detected value of skin pressure which is output from each pressure sensor. The operation determination unit 130 is also capable of outputting a control signal to each of the EMS electrodes.

Each pressure sensor detects skin pressure in response to receipt of a control signal from the operation determination unit 130, and returns the detected value of skin pressure (hereinafter referred to as the "detected pressure value") to the operation determination unit 130.

The information storage unit 120 stores a coefficient matrix that indicates the correlation between the detected pressure values (hereinafter referred to as the "pressure detection data") of the first to M-th pressure sensors $232_1$ to $232_M$ and the EMS electrodes 233 to be activated to promote the body to be maintained in the ideal posture by the body itself (hereinafter referred to as an "electrode activation pattern").

The coefficient matrix is generated in advance as a result of, for example, experiment-based learning, and is stored in the information storage unit 120. The details of the procedure for generating the coefficient matrix will be described below.

The operation determination unit 130 activates the first to M-th pressure sensors $232_1$ to $232_M$, and obtains the respective detected pressure values of the first to M-th pressure sensors $232_1$ to $232_M$ which will be returned. The operation determination unit 130 determines the electrode activation pattern of the first to N-th EMS electrode pairs $234_1$ to $234_N$ from the obtained detected pressure values, by using the coefficient matrix stored in the information storage unit 120. Then, the operation determination unit 130 activates the first to N-th EMS electrode pairs $234_1$ to $234_N$ in accordance with the determined electrode activation pattern.

Each of the first to N-th EMS electrode pairs $234_1$ to $234_N$ operates in response to a control signal from the operation determination unit 130.

Coefficient Matrix Generation Procedure

As described above, the coefficient matrix is information indicating the correlation between the pressure detection data and an electrode activation pattern for promoting the body to be maintained in the ideal posture by the body itself. The coefficient matrix may be statistically obtained from, for example, a plurality of correlations between pressure detection data and muscle conditions, which are determined for a plurality of subjects whose muscle conditions are known.

FIG. 8 is a diagram illustrating an example of data of a plurality of muscle conditions (hereinafter referred to as the "learning-specific muscle-condition data") for each of L subjects.

As illustrated in FIG. 8, learning-specific muscle-condition data 310 is data indicating the muscle conditions of a plurality of muscles for each of the first to L-th subjects. Each of the muscle conditions is scored "1" or "0" with "1" indicating that the muscle strength to maintain the ideal posture is sufficient and "0" indicating that the muscle strength to maintain the ideal posture is insufficient.

The determination as to whether the strength of each muscle is sufficient or insufficient is based on, for example, a result of palpation by a trained professional such as a physician or a result of measurement using a muscle hardness meter. Note that some subjects have well-balanced, strong muscles, and other subjects have muscles that are weak but well balanced. It is thus desirable that the determination as to whether or not the strength of each muscle is sufficient be made taking into account the strength of the surrounding muscles.

A muscle having insufficient strength to maintain the ideal posture is a muscle to be exercised, or a muscle to be stimulated by using an EMS electrode pair.

For example, the first subject has an insufficient latissimus dorsi muscle. For the first subject, the latissimus dorsi muscle is a muscle to be stimulated by using an EMS electrode pair.

FIG. 9 is a diagram illustrating an example of correspondence relationships between muscles and EMS electrodes (hereinafter referred to as the "muscle-to-electrode correspondence").

As illustrated in FIG. 9, in a muscle-to-electrode correspondence 320, each of a plurality of muscles is associated with one or more EMS electrode pairs. Here, an EMS electrode pair 234 associated with a particular muscle is an EMS electrode pair 234 located at the position where the particular muscle is stimulated while the posture correction apparatus 100 is worn. For example, the latissimus dorsi muscle is associated with the first to fourth EMS electrode pairs.

By integrating the learning-specific muscle-condition data 310 illustrated in FIG. 8 and the muscle-to-electrode correspondence 320 illustrated in FIG. 9, it is possible to obtain a matrix (hereinafter referred to as the "learning-specific operation necessity matrix") indicating a correspondence relationship between each subject and an EMS electrode pair to be activated for muscle stimulation.

FIG. 10 is a diagram illustrating an example of the learning-specific operation necessity matrix.

As illustrated in FIG. 10, a learning-specific operation necessity matrix 330 has rows respectively representing the first to N-th EMS electrode pairs $234_1$ to $234_N$, and columns respectively representing the first to L-th subjects. That is, the learning-specific operation necessity matrix 330 is an N×L matrix. Each component of the learning-specific operation necessity matrix 330 is scored "1" or "0" with "1" indicating that muscle stimulation is not necessary and "0" indicating that muscle stimulation is necessary.

For example, as described above, the first subject has an insufficient latissimus dorsi muscle, and the latissimus dorsi muscle is associated with the first to fourth EMS electrode pairs $234_1$ to $234_4$. Thus, for the first subject, it is necessary to activate the first to fourth EMS electrode pairs $234_1$ to $234_4$ for muscle stimulation.

In this manner, each of the first to L-th subjects for which necessity of muscle stimulation is determined for each muscle (i.e., for each EMS electrode pair) is caused to wear the posture correction apparatus 100 (or any other posture correction apparatus having substantially the same configuration), and the corresponding one or more of the first to M-th pressure sensors $232_1$ to $232_M$ are activated. Then, pressure detection data is collected, and thus a matrix indicating a correspondence relationship between each subject and a skin pressure pattern (hereinafter referred to as the "learning-specific pressure value matrix") can be obtained.

FIG. 11 is a diagram illustrating an example of the learning-specific pressure value matrix.

As illustrated in FIG. 11, a learning-specific pressure value matrix 340 has rows respectively representing the first to M-th pressure sensors $232_1$ to $232_M$, and columns respectively representing the first to L-th subjects. That is, the learning-specific pressure value matrix 340 is an M×L matrix.

For example, a number of pieces of pressure detection data "$PD1_1, PD2_1, \ldots, PDM_1$" are obtained for the first subject. As described above, the first subject has an insufficient latissimus dorsi muscle, and the first to fourth EMS electrode pairs $234_1$ to $234_4$ need to be activated for muscle stimulation. Thus, there is presumably a correlation between the pressure detection data of the first subject and the insufficiency of the strength of the latissimus dorsi muscle, that is, between the pressure detection data of the first subject and the need for muscle stimulation using the first to fourth EMS electrode pairs $234_1$ to $234_4$ (electrode activation pattern).

It is assumed that the above correlation can be represented by a coefficient matrix A in Expression (1) below, where O denotes the learning-specific operation necessity matrix 330 and X denotes the learning-specific pressure value matrix 340. In addition, the coefficient matrix A is an N×M matrix.

$$O = AX \qquad (1)$$

By modifying Expression (1), the coefficient matrix A can be represented by Expression (2) below using the learning-specific operation necessity matrix O and the learning-specific pressure value matrix X.

$$A = OX^{-1} \qquad (2)$$

FIG. 12 is a diagram illustrating an example of a coefficient matrix calculated from the learning-specific operation necessity matrix 330 and the learning-specific pressure value matrix 340.

Here, as illustrated in FIG. 12, a coefficient matrix 350 includes $a_{ij}$ (i=1, 2, \ldots, N; and j=1, 2, \ldots, M) as elements for the respective combinations of EMS electrode pairs 234 and pressure sensors 232.

For example, it is assumed that a subject in whom a muscle associated with the n-th EMS electrode $233_n$ is weak has a tendency to have a higher value of the m-th pressure sensor $232_m$ than other subjects. In this case, for a user who has a high value of the m-th pressure sensor $232_m$, it is desirable that the n-th EMS electrode $233_n$ be activated for muscle stimulation. The magnitude of the value of each element $a_{ij}$ of the coefficient matrix A is associated with the level of correlation between the detected value of one of the EMS electrodes 233 and the detected value of one of the pressure sensors 232.

Here, a number of pieces of pressure detection data of a user are arranged vertically in the same order as the order in the column corresponding to each of the pressure sensors 232 in the coefficient matrix 350. Accordingly, an M×1 column vector (hereinafter referred to as the "pressure detection data vector") is obtained, which is represented by sign "V".

The operation determination unit 130 calculates an evaluation value vector Y by, for example, performing the computation corresponding to Expression (3) below.

$$Y = AV \quad (3)$$

The evaluation value vector Y is an N×1 matrix with the N elements sequentially corresponding to the first to N-th EMS electrode pairs $234_1$ to $234_N$. Given that the j-th element of the pressure detection data vector V is expressed by sign "$v_j$", the i-th element $y_i$ of the evaluation value vector Y is represented by Expression (4) below.

$$y_i = a_{i1}v_1 + a_{i2}v_2 + \ldots + a_{iM}v_M \quad (4)$$

The value of each element $v_j$ of the pressure detection data vector V corresponds to the magnitude of the detected value of one of the pressure sensors 232 obtained from the user. As described above, the value of each element $a_{ij}$ of the coefficient matrix A is associated with the level of correlation between the detected value of one of the EMS electrodes 233 and the detected value of one of the pressure sensors 232. Thus, the i-th element $y_i$ of the evaluation value vector Y has a value corresponding to the degree of the intensity of the muscle stimulation to be output from the associated i-th EMS electrode $233_i$, or corresponding to the degree of need to activate the associated i-th EMS electrode $233_i$.

For example, the higher the need to activate the i-th EMS electrode $233_i$, the closer to "1" the value of the i-th element $y_i$ of the evaluation value vector Y is. On the other hand, the lower the need to activate the i-th EMS electrode $233_i$, the closer to "0" the value of the i-th element $y_i$ of the evaluation value vector Y is.

Accordingly, the operation determination unit 130 determines whether or not to activate each of the EMS electrode pairs 234 for muscle stimulation in accordance with the magnitude of the value of an element of the evaluation value vector Y.

For example, the operation determination unit 130 compares the value of each element $y_i$ of the evaluation value vector Y with a predetermined threshold value (for example, 0.5). Then, the operation determination unit 130 determines that an EMS electrode 233 corresponding to an element whose value is greater than or equal to the threshold value is activated for muscle stimulation, and determines that an EMS electrode 233 corresponding to an element whose value is less than the threshold value is not activated for muscle stimulation.

The coefficient matrix A may not necessarily indicate the correlation between pressure detection data and an electrode activation pattern, and may indicate the correlation between pressure detection data and a pattern of the muscles or body parts to be exercised to improve muscle strength. In this case, the operation determination unit 130 determines an electrode activation pattern by also using a table or the like that defines the muscle-to-electrode correspondence 320 illustrated in FIG. 9.

The posture correction apparatus 100 having the configuration described above may provide accurate muscle training so that the body can be maintained in a predetermined posture by using its own muscle strength.

Although not illustrated in the drawings, the posture correction apparatus 100 includes a power supply unit, an operation unit including key switches and the like, and a plurality of temperature sensors. The power supply unit supplies power to activate the CPU described above and the sheet device 230. The operation unit receives various operations from the user. The temperature sensors are disposed at a plurality of locations on the sheet member 231 so as to be buried in a manner similar to that of the pressure sensors 232, and are each configured to detect the temperature of the skin (hereinafter referred to as the "skin temperature") at the corresponding one of the plurality of locations. The power supply unit, the operation unit, and the temperature sensors are each connected to the operation determination unit 130 using a cable.

Each of the temperature sensors operates in response to receipt of a control signal from the operation determination unit 130, and reruns a detected value of skin temperature. In this embodiment, by way of example, each of the temperature sensors is located at least at a position where the temperature of the skin near each muscle, that is, the skin temperature indicating the degree of heat generated by each muscle, is detectable. Examples of the temperature sensors may include a temperature sensor that includes an organic thin film transistor having an organic molecular layer that is fabricated using a phthalocyanine nano structure (Japanese Unexamined Patent Application Publication No. 2007-178256).

The operation determination unit 130 controls the muscle stimulation to be provided to the body, based on the detected values of skin temperature. More specifically, muscle stimulation is stopped at the time when the skin temperature increases to some extent due to the muscle stimulation.

Operation of Posture Correction Apparatus

Next, a description will be given of the operation of the posture correction apparatus 100.

Figure 13:
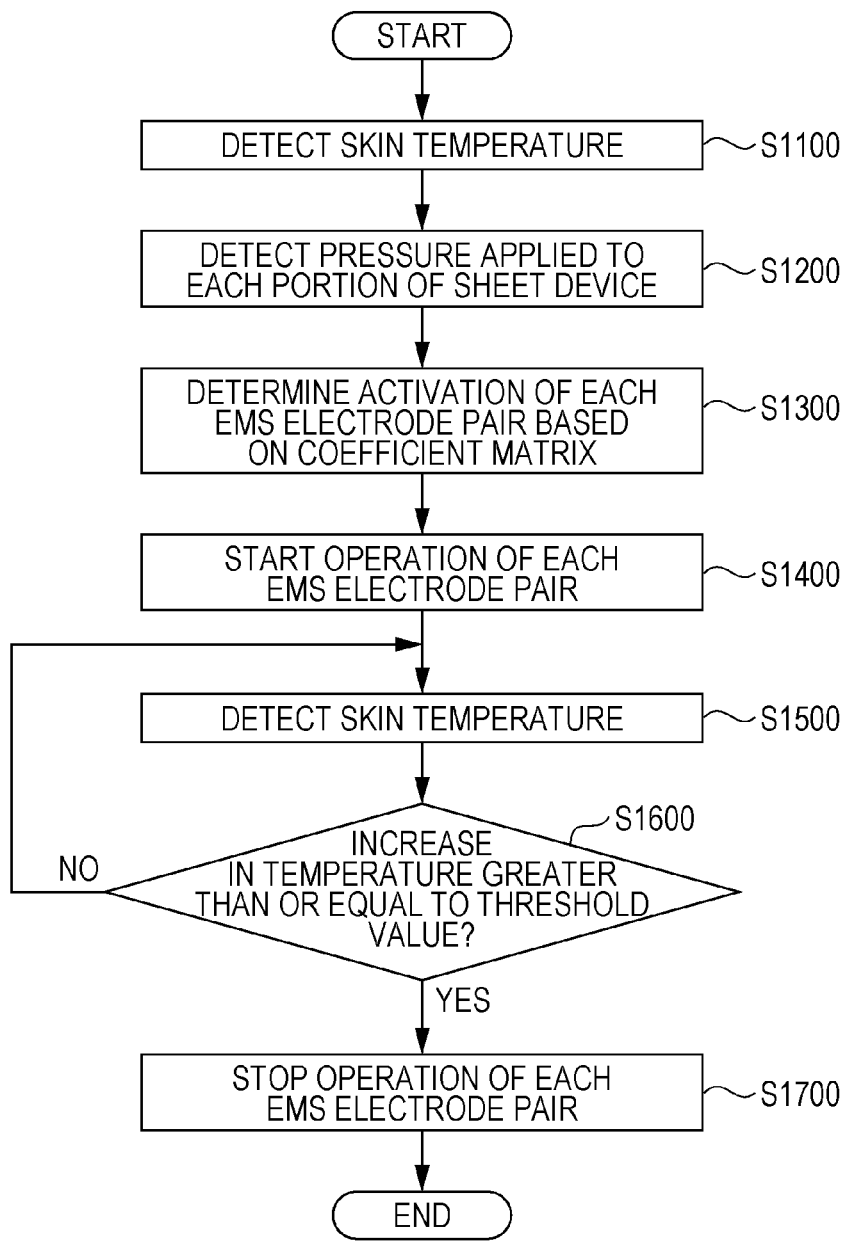
FIG. 13 is a flowchart illustrating an example of the operation of the posture correction apparatus according to the second embodiment.

FIG. 13 is a flowchart illustrating an example of the operation of the posture correction apparatus 100.

When a user performs an operation to give an instruction to start the operation of the posture correction apparatus 100 while the posture correction apparatus 100 is worn on the body of the user, the following process is started.

First, in step S1100, each of the plurality of temperature sensors detects a skin temperature before muscle stimulation begins, and outputs the detected value to the operation determination unit 130. The operation determination unit 130 stores the input temperature detected values.

Then, in step S1200, the muscle condition obtaining unit 110 detects pressures applied to the respective portions of the sheet device 230 by using the first to M-th pressure sensors $232_1$ to $232_M$, and outputs pressure detection data to the operation determination unit 130. In other words, the pressure detection data is information indicating a muscle condition in the body while the posture correction apparatus 100 is worn on the body.

Then, in step S1300, the operation determination unit 130 determines the activation of each of the EMS electrode pairs 234 (an electrode activation pattern) using the pressure detection data, based on the coefficient matrix 350 stored in the information storage unit 120 (see FIG. 12). In other words, the electrode activation pattern of the plurality of EMS electrode pairs 234 is information indicating which muscles to stimulate and how the muscles are stimulated in order to promote the body to be maintained in the ideal posture by the body itself.

Then, in step S1400, the first to N-th EMS electrode pairs $234_1$ to $234_N$ of the muscle stimulation unit 140 start the operation in accordance with the determined electrode activation pattern. For example, some of the EMS electrodes 233 start stimulating muscles, and others of the EMS electrodes 233 do not start stimulating muscles.

The output intensity of the current, that is, the degree of the intensity of muscle stimulation, may have, for example, a fixed value for all the EMS electrode pairs 234. For example, each of the EMS electrode pairs 234 performs the following process every 0.2 seconds. The process includes discharging the current less than 1 ampere at a voltage of approximately 25 volts intermittently several times at intervals of 20 milliseconds for as short a time period as, for example, approximately 20 microseconds. The degree of the intensity of muscle stimulation may also be variable. For example, if it is determined that a given muscle is particularly weak, the operation determination unit 130 sets a current value or a duty ratio to a value smaller than a default value (fixed value) or sets the period during which current is flowing to a value longer than a default value in order to reduce the load on the given muscle. When the muscle is strengthened properly, the operation determination unit 130 switches the setting from the low-load mode described above to a normal mode (default value).

Then, in step S1500, each of the plurality of temperature sensors detects a skin temperature, and outputs the detected value to the operation determination unit 130. That is, the posture correction apparatus 100 detects skin temperatures after muscle stimulation begins.

Then, in step S1600, the operation determination unit 130 determines whether or not the increase in skin temperature from the beginning of muscle stimulation is greater than or equal to a predetermined threshold value. The threshold value is a value corresponding to a change in skin temperature when sufficient, but not excessive, muscle stimulation is applied, and may be equal to, for example, 1°.

When the increase in skin temperature is less than the threshold value (NO in S1600), the operation determination unit 130 returns the process to step S1500. That is, the processing of steps S1500 and S1600 is repeatedly performed until the increase in skin temperature from the beginning of muscle stimulation has reached the threshold value.

When the increase in skin temperature is greater than or equal to the threshold value (YES in S1600), the operation determination unit 130 advances the process to step S1700.

In step S1700, the first to N-th EMS electrode pairs $234_1$ to $234_N$ of the muscle stimulation unit 140 stop their operation. Then, the series of processes ends.

Through the operation described above, the posture correction apparatus 100 may provide accurate muscle training so that the body can be maintained in a predetermined posture by using its own muscle strength. In addition, the posture correction apparatus 100 stops stimulating muscles at the time when the skin temperature increases to some extent, preventing overload on the muscles. Since a malfunction of the posture correction apparatus 100 may cause an increase in temperature, the stopping of muscle stimulation based on comparison between the skin temperature and a predetermined threshold value will contribute to the safety of the product.

Advantages of Posture Correction Apparatus

As described above, the posture correction apparatus 100 according to this embodiment may provide accurate muscle training so that the body can be maintained in a predetermined posture by using its own muscle strength.

Posture is maintained by cooperation of a plurality of muscles. Thus, strengthening only a particular muscle may cause an imbalance of the plurality of muscles, resulting in a need to strengthen the other muscles as a relative consequence. In this regard, the posture correction apparatus 100 according to this embodiment may provide accurate muscle stimulation to a plurality of muscles, resulting in balanced strengthening of the plurality of muscles.

As described above, exercising muscles necessary to maintain the body in good posture by using its own muscle strength may result in a reduction in facial sagging. Accordingly, the posture correction apparatus 100 according to this embodiment may reduce facial sagging.

In addition, at least some of the weakened muscles which may cause poor posture are exercised, enabling, as a relative consequence, indirect exercising of the other muscles that need to be strengthened. Accordingly, the posture correction apparatus 100 allows balanced exercising of all the muscles necessary to maintain the ideal posture.

Furthermore, the sheet device 230 is thin and elastic. Due to these features, the user can wear the posture correction apparatus 100 with a similar feeling to that of wearing a conventional posture correction apparatus, and the presence of the sheet device 230 may be inconspicuous.

Furthermore, the posture correction apparatus 100 according to this embodiment may promote the flow of blood and circulation lymphatic fluid through the muscles to be exercised and the area around the muscles. Accordingly, in addition to strengthening of muscles, anti-aging effects due to the improved circulation of blood and lymphatic fluid may also be achieved.

Users whose postures are to be corrected may include elderly people and persons with weak muscles. For such users, muscle stimulation at even an appropriate intensity (or for an appropriate period of time) for general users would be excessive. To avoid this risk, it is desirable that the posture correction apparatus 100 sequentially detect muscle conditions while stimulating muscles, and stop stimulating the muscles before the muscles are excessively stimulated.

For example, the operation determination unit 130 causes the first to M-th pressure sensors $232_1$ to $232_M$ to continuously operate during muscle stimulation (for a period during which steps S1500 and S1600 in FIG. 13 are repeatedly performed). Then, the operation determination unit 130 sequentially performs the operation of obtaining the pressure detection data vector V and calculating the evaluation value vector Y. The evaluation value vector Y can be computed for a moment since the computation is simple, as given in Expression (3). Thus, the posture correction apparatus 100 can stop stimulating, at any time, muscles whose strength has been improved during muscle stimulation.

Third Embodiment

The detected pressure values obtained in the second embodiment are not likely to reflect a reduction in the strength of muscles that have started to weaken. That is, in the second embodiment, it may be difficult to appropriately stimulate weakening muscles, and a user would fail to sufficiently reduce facial sagging.

There is a correlation between an actual posture of the body and which muscles to start to weaken and how much they weaken, that is, between an actual posture of the body and a plurality of muscle conditions.

A third embodiment of the present disclosure will be described, by way of example, in which an electrode activation pattern is determined not only based on pressure detection data but also based on an actual posture of the body.

Configuration of Posture Correction Apparatus

Figure 14:
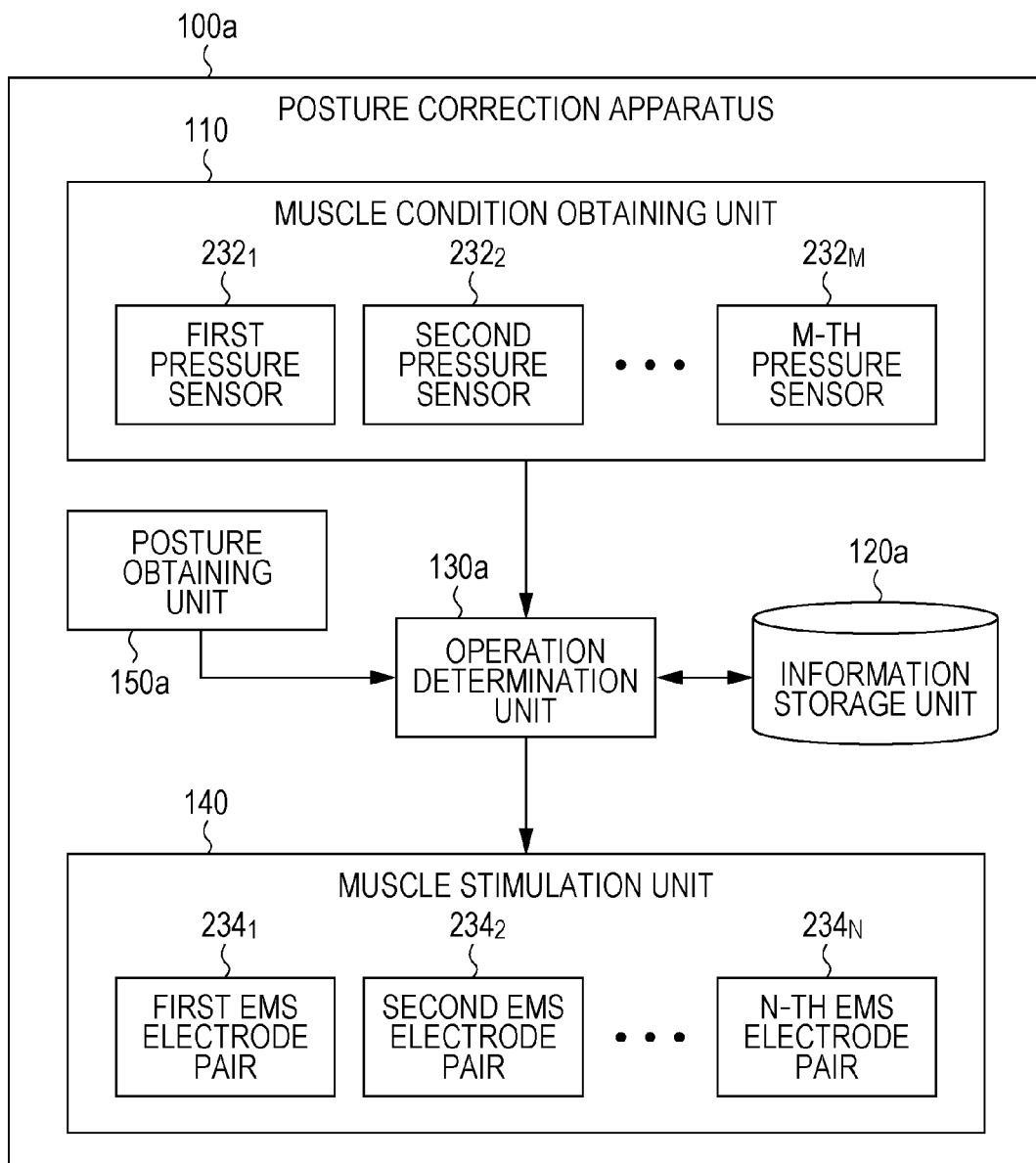
FIG. 14 is a diagram illustrating an example functional configuration of a posture correction apparatus according to a third embodiment of the present disclosure.

FIG. 14 is a diagram illustrating an example functional configuration of a posture correction apparatus according to this embodiment, and corresponds to FIG. 7 illustrating the second embodiment. The same or substantially the same portions as those in FIG. 7 are assigned the same reference numerals, and a description thereof is omitted.

In FIG. 14, a posture correction apparatus 100a further includes a posture obtaining unit 150a. The posture correction apparatus 100a also includes an information storage unit 120a and an operation determination unit 130a in place of the information storage unit 120 and the operation determination unit 130 of the second embodiment.

The posture obtaining unit 150a detects information related to a posture of the body. More specifically, the posture obtaining unit 150a obtains, for example, an image of the body which was shot using a camera from the front (hereinafter referred to as the "front image"), and an image of the body which was shot from the side (hereinafter referred to as the "side image"). Then, the posture obtaining unit 150a analyzes the obtained front image and side image (hereinafter collectively referred to as the "captured images"), and obtains posture parameters indicating the actual posture of the body.

The posture parameters are not particularly limited so long as the conditions of body postures of multiple unspecified people can be quantified. The posture parameters include, for example, information indicating the arrangement of points of observation on the captured images for predetermined portions of the body.

Figure 15A:
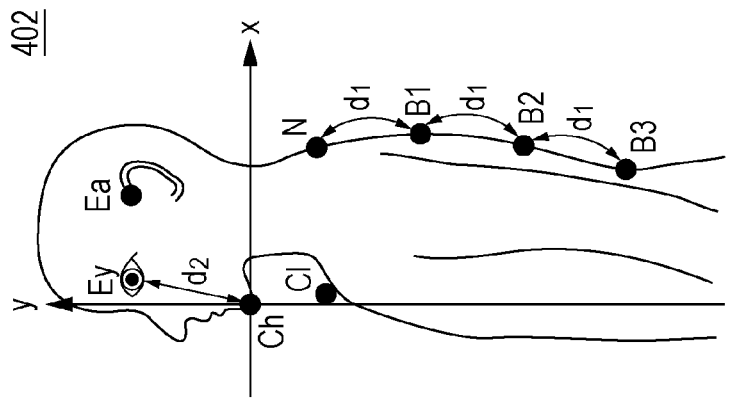
FIGS. 15A and 15B are diagrams illustrating an example of points of observation in the third embodiment.
Figure 15B:
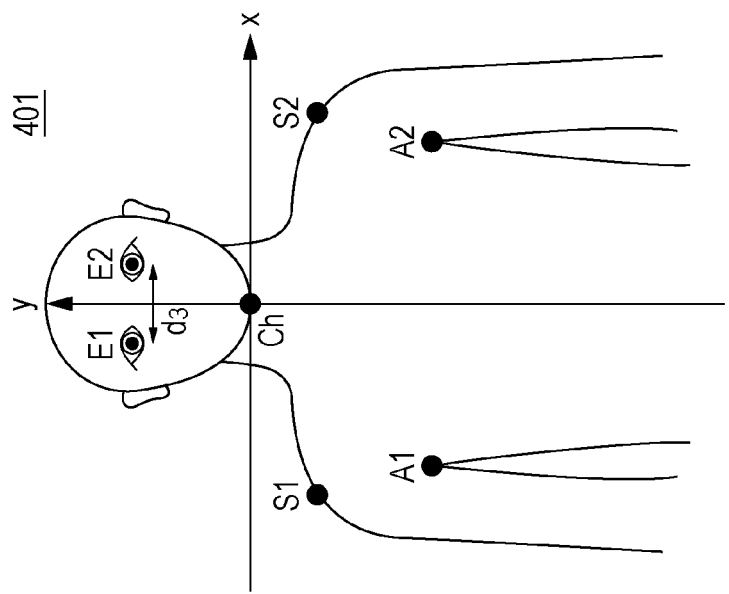

FIGS. 15A and 15B are diagrams illustrating an example of a plurality of points of observation extracted from the captured images. FIG. 15A illustrates the points of observation obtained from the front image. FIG. 15B illustrates the points of observation obtained from the side image.

As illustrated in FIG. 15A, the posture obtaining unit 150a obtains, from a front image 401, a chin position (Ch), a right shoulder position (S1), a left shoulder position (S2), a right armpit position (A1), a left armpit position (A2), a right eye position (E1), and a left eye position (E2) on the front image 401.

Furthermore, as illustrated in FIG. 15B, the posture obtaining unit 150a obtains, from a side image 402, a chin position (Ch), an eye position (Ey), an ear position (Ea), a clavicle position (Cl), and a cervical vertebra position (N) on the side image 402. The posture obtaining unit 150a further obtains three points that are spaced an equal distance (d1), that is, an upper back position (B1), a middle back position (B2), and a lower back position (B3), from the side image 402.

The posture obtaining unit 150a obtains the positions of the parts described above from the captured images by using known image analysis such as pattern matching.

The posture obtaining unit 150a defines, on the front image 401, an x-y coordinate system with, for example, the chin position (Ch) on the front image 401 as the origin, the x axis as horizontal, and the y axis as vertical, for which the unit of measure is based on the distance (d3) between both eyes (irises). The posture obtaining unit 150a further defines, on the side image 402, an x-y coordinate system with, for example, the chin position (Ch) on the side image 402 as the origin, the x axis as horizontal, and the y axis as vertical, for which the unit of measure is based on the distance (d2) between the chin position (Ch) and the iris.

Then, the posture obtaining unit 150a obtains, from the obtained coordinate values of the respective parts, a plurality of predetermined posture parameters, examples of which include the ratio of the difference in x coordinate value between the chin position (Ch) and the right shoulder position (S1) to the difference in x coordinate value between the chin position (Ch) and the left shoulder position (S2).

The obtained posture parameter group (hereinafter referred to as the "posture detection data") reflects the features of a posture of the capture subject. That is, the posture detection data has content corresponding to the locations of weak muscles.

Accordingly, the operation determination unit 130a determines an electrode activation pattern not only based on pressure detection data but also based on posture detection data.

Electrode Activation Pattern Determination Procedure

Specifically, the following operation is performed. The information storage unit 120a in this embodiment stores in advance not only the coefficient matrix A described with reference to the second embodiment but also a coefficient matrix B indicating the correlation between posture detection data and an electrode activation pattern.

Similarly to the coefficient matrix A, for example, the coefficient matrix B is statistically obtained from a plurality of correlations between posture detection data including first to K-th posture parameters and muscle conditions, which are determined for the first to L-th subjects whose muscle conditions are known.

It is desirable that subjects be photographed for the generation of the coefficient matrix B while the subjects are not wearing the posture correction apparatus 100a, and it is desirable that a user be photographed for the determination of an actual operation in an electrode activation pattern while the user is not wearing the posture correction apparatus 100a. In the photographing of subjects and a user, real poor posture of the body, which is not maintained in the ideal posture by the posture correction apparatus 100a, is detected.

Here, it is assumed that the coefficient matrix B is an N×K matrix including $b_{ih}$ (i=1, 2, . . . , N; and h=1, 2, . . . , K) as elements for the respective combinations of EMS electrode pairs 234 and posture parameter types.

For example, it is assumed that a subject in whom a muscle associated with the n-th EMS electrode $233_n$ is weak has a tendency to have a higher value of the k-th posture parameter than other subjects. In this case, for a user who has a high value of the k-th posture parameter, it is desirable that the n-th EMS electrode $233_n$ be activated for muscle stimulation. The magnitude of the value of each element $b_{ih}$ of the coefficient matrix B is associated with the level of correlation between the detected value of one of the EMS electrodes 233 and the value of one of the posture parameters.

Here, posture parameters of posture detection data of a user are arranged vertically in the same order as the order in the item of each of the posture parameters obtained when the coefficient matrix B is generated. Accordingly, a K×1 column vector (hereinafter referred to as the "posture detection data vector") is obtained, which is represented by sign "W".

The operation determination unit 130a calculates a posture evaluation value vector Z by, for example, performing the computation corresponding to Expression (5) below.

$$Z = BW \qquad (5)$$

The evaluation value vector Z is an N×1 matrix with the N elements sequentially corresponding to the first to N-th EMS electrode pairs $234_1$ to $234_N$. Given that the i-th element of the evaluation value vector Z is expressed by sign "$z_i$", the i-th element $z_i$ of the evaluation value vector Z is represented by Expression (6) below.

$$z_i = b_{i1}z_1 + b_{i2}z_2 + \ldots + b_{iK}z_K \qquad (6)$$

Then, the operation determination unit 130a uses, as a final evaluation value vector $Y_{fin}$, an N×1 row vector obtained by taking the average of the evaluation value vector Z and the evaluation value vector Y calculated using a procedure similar to that in the second embodiment. That is, the i-th element $y_{fin\_i}$ of the final evaluation value vector $Y_{fin}$ is represented by Expression (7) below.

$$y_{fin\_i} = (y_i + z_i)/2 \qquad (7)$$

The operation determination unit 130a may calculate a final evaluation value vector $Y_{fin}$ by taking the weighted average. In this case, the operation determination unit 130a may change the weight by which the value of the evaluation value vector Z is multiplied and the weight by which the value of the evaluation value vector Y is multiplied, in accordance with the difference in the quality and the like of captured images.

Then, similarly to the second embodiment, the operation determination unit 130a determines an electrode activation pattern by comparing the value of each element $y_{fin\_i}$ of the final evaluation value vector $Y_{fin}$ with a predetermined threshold value (for example, 0.5), and controls the operation of each of the EMS electrode pairs 234.

Advantages of Posture Correction Apparatus

The posture correction apparatus 100a having the configuration described above can determine an electrode activation pattern not only based on pressure detection data but also based on the actual body posture of the user. That is, the determination of an electrode activation pattern according to the second embodiment may be adjusted based on the posture detection data.

Accordingly, the posture correction apparatus 100a may also appropriately stimulate muscles that have started to weaken. That is, the posture correction apparatus 100a may more reliably reduce facial sagging.

The posture correction apparatus 100a may determine an electrode activation pattern based on posture detection data without using pressure detection data. However, depending on the accuracy of posture detection, the use of posture detection data in combination with pressure detection data may allow more accurate muscle stimulation.

Fourth Embodiment

There is a correlation between a plurality of muscle conditions in the body and the condition of facial sagging. A fourth embodiment will be described, by way of example, in which an electrode activation pattern is determined not only based on pressure detection data but also based on the actual condition of facial sagging.

Configuration of Posture Correction Apparatus

Figure 16:
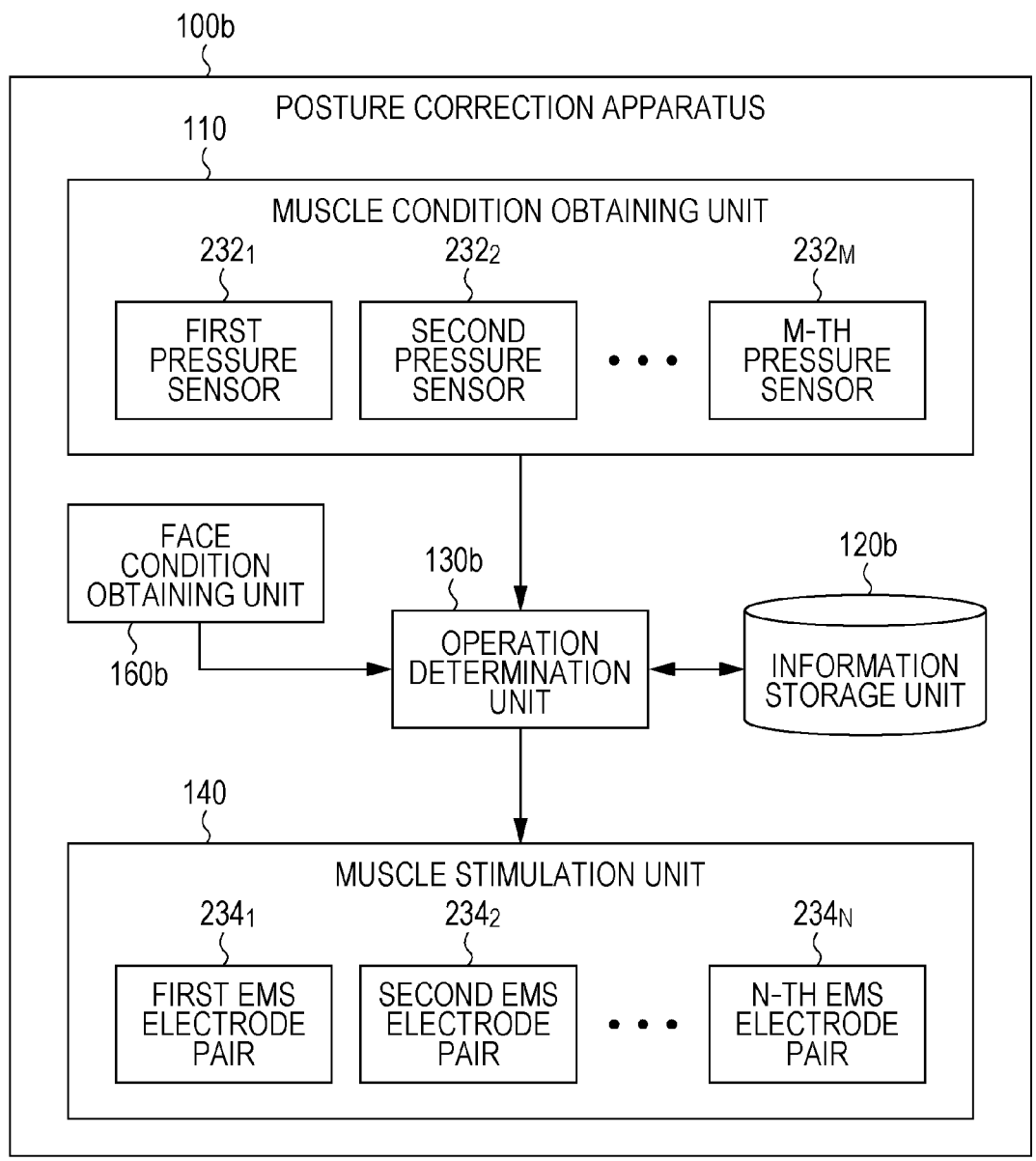
FIG. 16 is a diagram illustrating an example functional configuration of a posture correction apparatus according to a fourth embodiment of the present disclosure.

FIG. 16 is a diagram illustrating an example functional configuration of a posture correction apparatus according to this embodiment, and corresponds to FIG. 7 illustrating the second embodiment. The same or substantially the same portions as those in FIG. 7 are assigned the same reference numerals, and a description thereof is omitted.

In FIG. 16, a posture correction apparatus 100b further includes a face condition obtaining unit 160b. The posture correction apparatus 100b also includes an information storage unit 120b and an operation determination unit 130b in place of the information storage unit 120 and the operation determination unit 130 of the second embodiment.

The face condition obtaining unit 160b obtains information related to a condition of facial sagging. More specifically, the face condition obtaining unit 160b detects the skin pressure as the information related to the condition of facial sagging by using, for example, a face sheet having a plurality of pressure sensors arranged thereon.

Figure 17B:
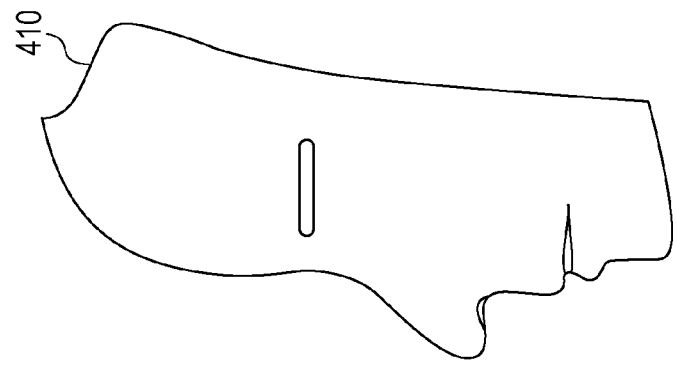
FIGS. 17A and 17B are diagrams illustrating an example external appearance of a face sheet in the fourth embodiment.
Figure 17A:
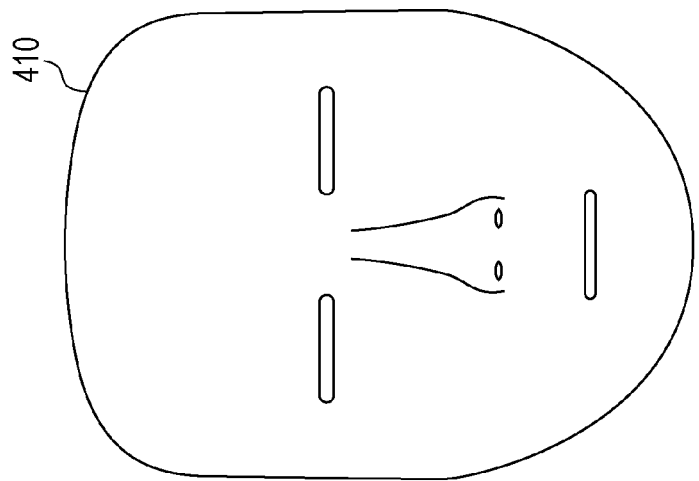

FIGS. 17A and 17B are diagrams illustrating an example external appearance of the face sheet. FIG. 17A illustrates an external appearance of the face sheet when viewed from the front. FIG. 17B illustrates an external appearance of the face sheet when viewed from the side.

As illustrated in FIGS. 17A and 17B, a face sheet 410 has a three-dimensional shape covering the surface of the face, and has cuts at positions corresponding to the eyes, nose, and mouth. The face sheet 410 is configured to, when placed at a predetermined position on the face, keep closely adhering to the entire surface of the skin of the face due to the surface tension. In order to secure the adhesion, biocompatible glue such as spirit gum, silicone adhesive, or latex adhesive may additionally be used. In addition, the size of the face sheet 410 is desirably selected from a plurality of sizes in accordance with the size of the face.

The face sheet 410 has a configuration similar to that of, for example, the sheet device 230 (see FIG. 4) described with reference to the second embodiment. The face sheet 410 includes pressure sensors (hereinafter referred to as "face pressure sensors") having a configuration similar to the pressure sensors 232, but does not include the EMS electrode pairs 234. Each face pressure sensor is disposed on a surface of the face sheet 410 that closely adheres to the face when the face sheet 410 is placed over the face, and is configured to detect the pressure (face pressure) between the facial skin and the face sheet 410.

Figure 18:
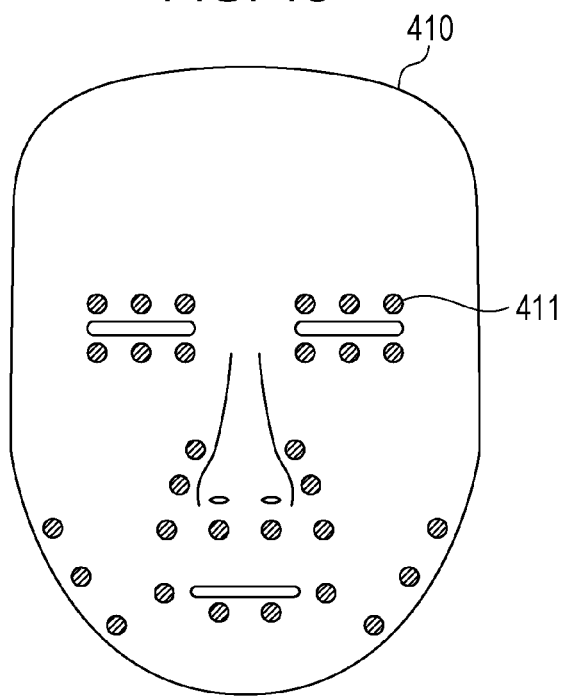
FIG. 18 is a diagram illustrating an example arrangement of face pressure sensors in the fourth embodiment.

FIG. 18 is a diagram illustrating an example arrangement of face pressure sensors, and corresponds to FIG. 17A.

As illustrated in FIG. 18, a plurality of face pressure sensors 411 are arranged along portions corresponding to the upper eyelids, the lower eyelids, regions where nasolabial folds develop, the area surrounding the mouth, and the outline of the cheeks. The above regions are regions where a reduction in the strength of facial muscles may cause facial sagging to be likely to occur. The above regions are also regions where instant elimination of sagging is achievable by tensing facial muscles such as by raising the eyebrows and the corners of the mouth.

Here, by way of example, P face pressure sensors 411 are arranged on the face sheet 410. Each of the P face pressure sensors 411 is connected to the operation determination unit 130b via a cable (not illustrated). That is, the operation determination unit 130b is configured to output a control signal to each of the face pressure sensors 411 and receive, as input, a detected value of skin pressure which is output from each of the face pressure sensors 411. The operation determination unit 130b may communicate information to each of the P face pressure sensors 411 or to a communication unit (not illustrated) disposed on the face sheet 410 via wireless communication.

The P face pressure sensors 411 constitute the face condition obtaining unit 160b. The face condition obtaining unit 160b detects skin pressures at the respective locations on the face both in the state where facial muscles are relaxed (hereinafter referred to as the "normal state") and in the state where predetermined muscles in the face are tensed (hereinafter referred to as the "tension state"), for example, the state where the eyebrows are raised as much as possible. The tension state is a state where the frontalis muscle, the galea aponeurotia, and the occipitalis muscle, and so forth contract, which results in elimination, or at least reduction, of facial sagging that occurs on the upper eyelids, the lower eyelids, nasolabial folds, the cheeks, and so forth. Then, the face condition obtaining unit 160b outputs the pressure detection data obtained in the normal state and the pressure detection data obtained in the tension state to the face condition obtaining unit 160b.

The face condition obtaining unit 160b obtains, as a face condition parameter, a difference between the pressure detection data in the normal state and the pressure detection data in the tension state for each of the face pressure sensors 411. The difference in pressure detection data generally increases as the degree to which the facial skin is sagging increases. That is, the obtained face condition parameter group (hereinafter referred to as the "face condition detection data") reflects the features of facial sagging. That is, the face condition detection data has content corresponding to the locations of weak muscles in the face. In addition, as described above, the strength of the facial muscles is closely related to the strength of the muscles in the body.

Accordingly, the operation determination unit 130b determines an electrode activation pattern not only based on pressure detection data but also based on face condition detection data.

The face condition parameters are not particularly limited so long as the conditions of sagging of the facial skins of multiple unspecified people can be quantified.

Electrode Activation Pattern Determination Procedure

Specifically, the following operation is performed. The information storage unit 120b in this embodiment stores in advance not only the coefficient matrix A described with reference to the second embodiment but also a coefficient matrix C indicating the correlation between face condition detection data and an electrode activation pattern.

Similarly to the coefficient matrix A, for example, the coefficient matrix C is statistically obtained from a plurality of correlations between face condition detection data including first to Q-th face condition parameters and muscle conditions in the body, which are determined for the first to L-th subjects whose muscle conditions are known.

Here, it is assumed that the coefficient matrix C is an N×Q matrix including $c_{ig}$ (i=1, 2, ..., N; and g=1, 2, ..., Q) as elements for the respective combinations of EMS electrode pairs 234 and face condition parameter types.

For example, it is assumed that a subject in whom a muscle associated with the n-th EMS electrode $233_n$ is weak has a tendency to have a higher value of the q-th face condition parameter than other subjects. In this case, for a user who has a high value of the q-th face condition parameter, it is desirable that the n-th EMS electrode $233_n$ be activated for muscle stimulation. The magnitude of the value of each element $c_{ig}$ of the coefficient matrix C is associated with the level of correlation between the detected value of one of the EMS electrodes 233 and the value of one face condition parameter.

Here, face condition parameters of face condition detection data of a user are arranged vertically in the same order as the order in the item of each of the face condition parameters obtained when the coefficient matrix C is generated. Accordingly, a Q×1 column vector (hereinafter referred to as the "face condition detection data vector") is obtained, which is represented by sign "T".

The operation determination unit 130b calculates a posture evaluation value vector U by, for example, performing the computation corresponding to Expression (8) below.

$$U = CT \quad (8)$$

The evaluation value vector U is an N×1 matrix with N elements sequentially corresponding to the first to N-th EMS electrode pairs $234_1$ to $234_N$. Given that the i-th element of the evaluation value vector U is expressed by sign "$u_i$", the i-th element $u_i$ of the evaluation value vector U is represented by Expression (9) below.

$$u_i = c_{i1}u_1 + c_{i2}u_2 + \ldots c_{iQ}u_Q \quad (9)$$

Then, the operation determination unit 130b uses, as a final evaluation value vector $Y_{fin}$, an N×1 row vector obtained by taking the average of the evaluation value vector U and the evaluation value vector Y calculated using a procedure similar to that in the second embodiment. That is, the i-th element $y_{fin\_i}$ of the final evaluation value vector $Y_{fin}$ is represented by Expression (10) below.

$$y_{fin\_i} = (y_i + u_i)/2 \quad (10)$$

Then, similarly to the second embodiment, the operation determination unit 130b determines an electrode activation pattern by comparing the value of each element $y_{fin\_i}$ of the final evaluation value vector $Y_{fin}$ with a predetermined threshold value (for example, 0.5), and controls the operation of each of the EMS electrode pairs 234.

The operation determination unit 130b may calculate a final evaluation value vector $Y_{fin}$ by taking the weighted average. In this case, the operation determination unit 130b may change the weight by which the value of the evaluation value vector U is multiplied and the weight by which the value of the evaluation value vector Y is multiplied, in accordance with the difference in facial sagging between individuals and the like.

Advantages of Posture Correction Apparatus

The posture correction apparatus 100b having the configuration described above can determine an electrode activation pattern not only based on pressure detection data of the body but also based on pressure detection data of the face, that is, the condition of sagging of the facial skin of a user. That is, the determination of an electrode activation pattern according to the second embodiment may be adjusted based on the face condition detection data.

Accordingly, the posture correction apparatus 100b may appropriately stimulate muscles in accordance with the actual facial sagging. That is, the posture correction apparatus 100b may more reliably reduce facial sagging.

The posture correction apparatus 100b may determine an electrode activation pattern based on face condition detection data without using pressure detection data of the body. However, in terms of improvement in posture, it is desirable to use face condition detection data and pressure detection data.

In addition, the configuration according to this embodiment may be used in combination with the configuration according to the third embodiment. In this case, the operation determination unit 130b uses, as a final evaluation value vector $Y_{fin}$, a value obtained by combining the evaluation value vectors Y, Z, and U based on, for example, the pressure detection data of the body, the posture detection data, and the face condition detection data.

In addition, the posture correction apparatus 100b may be configured such that the face sheet 410 further has arranged thereon EMS electrodes (hereinafter referred to as "face EMS electrodes") having a configuration similar to that of the EMS electrodes 233 according to the second embodiment.

Arrangement of EMS Electrodes

Figure 19:
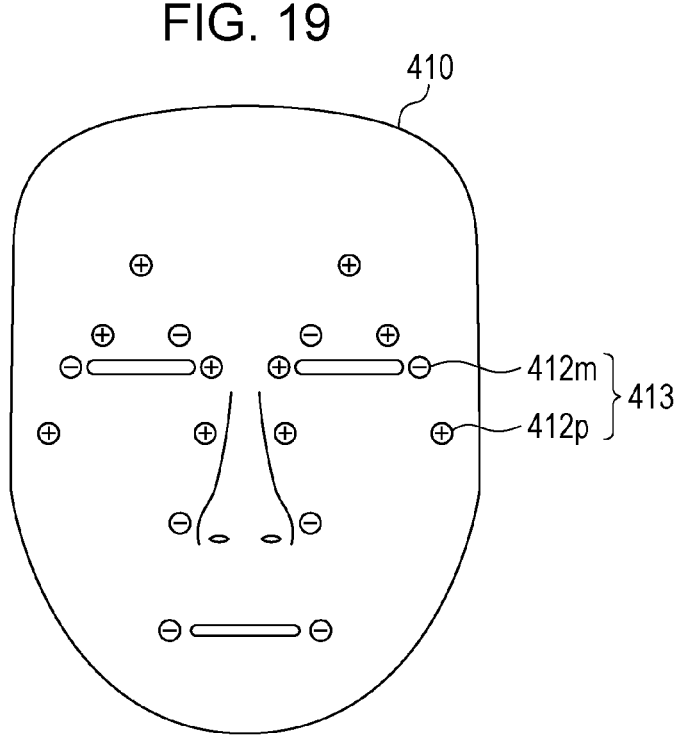
FIG. 19 is a diagram illustrating an example arrangement of face EMS electrodes in the fourth embodiment.

FIG. 19 is a diagram illustrating an example arrangement of face EMS electrodes, and corresponds to FIG. 17A.

In FIG. 19, the face sheet 410 has arranged thereon a plurality of face EMS electrode pairs 413 each composed of a plus (or positive) face EMS electrode $412_p$ and a minus (or negative) face EMS electrode $412_m$.

Each of the face EMS electrode pairs 413 is arranged so as to stimulate any of the muscles necessary to reduce facial sagging. Examples of the muscles necessary to reduce facial sagging include the frontalis muscle, the corrugator supercilii muscle, the orbicularis oculi muscle, the zygomaticus muscle, and the orbicularis oris muscle. Note that the output of the face EMS electrode pairs 413 is smaller than the output of the EMS electrode pairs 234, which are used for muscles in the body.

Some or all of the functions of an information storage unit and an operation determination unit according to each of the embodiments described above may be provided in a user accessible device separate from a posture correction supporter, such as a controller device or a mobile telephone. In a case where a controller device is used, it is desirable that a posture correction supporter and the controller device be detachably connected to each other via a connector and a cable. The above configuration allows a user to replace a posture correction supporter that is defective or no longer fits well with a new one.

The functions described above may also be provided in a server on a network. That is, some of the functions of the posture correction apparatus may be implemented using cloud computing services. In this case, an operation determination unit at least includes a communication unit, and transmits detection data to the server to ask the server for the content of the muscle stimulation to be provided to the body.

Furthermore, the coefficient matrix A may be generated in the posture correction apparatus 100. In this case, the posture correction apparatus 100 receives, as input, the learning-specific operation necessity matrix O and the learning-specific pressure value matrix X, and performs the computation represented by Expression (2).

The types of the feature values indicating a muscle condition in the body, a posture condition, and a condition of facial sagging, and the technique for detecting the above conditions are not limited to those in the examples described above.

For example, it has been found that an organic thin film transistor exhibits various electrical characteristics that originate from the molecular structure of organic molecules, and may form a variety of sensors including a gas ion sensor, a humidity sensor, a temperature sensor, an optical sensor, and a pressure sensor (see Japanese Patent No. 5197960 and Japanese Unexamined Patent Application Publication No. 2007-178256). Accordingly, the configurations and operations described with reference to the respective embodiments may be applied to the physical quantity related to gas ions, humidity, temperature, the amount of light, colors, and their associated parameters.

For example, desirably, when a posture correction apparatus obtains a muscle condition in the body while attached to a predetermined position on the body, the posture correction apparatus measures the tensions applied to a sheet member at individual positions, and obtains a pattern of the tensions at the respective positions as a muscle condition in the body. A device configured for such measurement of the tensions may be used to apply the configurations and operations described with reference to the respective embodiments to the tensions at the respective positions or their associated parameters. In the embodiments described above, feature values corresponding to the tensions are indirectly used as skin pressures.

The types of muscle stimulation and the types of the operation to be determined are not limited to those in the example described above. For example, a posture correction apparatus may be configured to stimulate each muscle by pressing the muscle using a piezoelectric element. In addition, the posture correction apparatus may be configured to, instead of merely controlling the on-off operation of each EMS electrode pair, control the intensity, time period, time interval, and rhythmic pattern of the current to be output, or the like in accordance with the muscle condition in the body, the posture condition, or the condition of facial sagging, which has been detected.

A posture correction apparatus according to an embodiment of the present disclosure includes an obtaining unit configured to obtain information related to a muscle condition in a body, a determination unit configured to determine muscle stimulation to be provided to the body, based on the obtained information, and a stimulation unit configured to provide the determined muscle stimulation to the body.

In the posture correction apparatus, the obtaining unit may be configured to obtain the information related to the muscle condition while being in contact with skin of the body, and the stimulation unit may be configured to provide the muscle stimulation to the body while being in contact with the skin.

In addition, in the posture correction apparatus, the obtaining unit may include a plurality of pressure sensors disposed at a plurality of locations on a sheet member, each of the pressure sensors being configured to detect a pressure between the sheet member and the skin as the information related to the muscle condition, and the determination unit may be configured to determine the muscle condition based on the pressure detected by the each of the pressure sensors. In addition, the stimulation unit may include a plurality of electrical muscle stimulation (EMS) electrode pairs disposed at a plurality of locations on the sheet member.

In addition, in the posture correction apparatus, the sheet member may be connected to the determination unit using a connector and a cable.

In addition, in the posture correction apparatus, the obtaining unit may be configured to obtain the information related to the muscle condition in each of a plurality of parts of the body, and the determination unit may be configured to determine the muscle stimulation to be provided separately to the plurality of parts based on the obtained information. In addition, the stimulation unit may be configured to provide the muscle stimulation separately to the plurality of parts of the body.

In addition, in the posture correction apparatus, the obtaining unit may further include a plurality of temperature sensors disposed at a plurality of locations on the sheet member, each of the plurality of temperature sensors being configured to detect a temperature of the skin at each of the plurality of locations, and the determination unit may be configured to control the muscle stimulation to be provided to the body, based on the detected temperature.

In addition, in the posture correction apparatus, the determination unit may be configured to stop the muscle stimulation in a case where the detected temperature exceeds a predetermined threshold value.

In addition, in the posture correction apparatus, the obtaining unit may be configured to obtain information related to a posture of the body, and the determination unit may be configured to determine the muscle stimulation to be provided to the body based on the obtained information related to the posture of the body.

In addition, the posture correction apparatus may further include a face sheet, and the obtaining unit includes a plurality of pressure sensors disposed at a plurality of locations on the face sheet, each of the pressure sensors being configured to detect a pressure between the face sheet and skin of the face as information related to a condition of sagging of the face, and the determination unit may be configured to determine the muscle stimulation to be provided to the body based on the detected pressure.

A posture correction method using a posture correction apparatus according to another embodiment of the present disclosure includes obtaining information related to a muscle condition in a body, determining muscle stimulation to be provided to the body, based on the obtained information, and providing the determined muscle stimulation to the body.

In exemplary embodiments, the present disclosure is suitable for use in a posture correction apparatus and a posture correction method that may allow a reduction in facial sagging.

What is claimed is:

1. A posture correction wear, comprising:
a plurality of pressure sensors disposed at a plurality of locations on the posture correction wear, the plurality of pressure sensors configured to detect pressures between the posture correction wear and a body of a user when the user wears the posture correction wear;
a plurality of electrical muscle stimulation electrode pairs disposed at a plurality of locations on the posture correction wear, the plurality of electrical muscle stimulation electrode pairs configured to apply electrical muscle stimulation to the body;
a plurality of temperature sensors disposed at a plurality of locations on the posture correction wear; and
a determiner that determines electrode operation patterns for the plurality of electrical muscle stimulation electrode pairs based on the pressures detected by the plurality of pressure sensors, and determines whether or not to stop the application of the electrical muscle stimulation based on temperatures detected by the plurality of temperature sensors, before and after the application of the electrical muscle stimulation.

2. A posture correction wear according to claim 1, further comprising:
a posture obtainer that is configured to obtain images of the user including a front image of the user, and is configured to generate posture parameters, including a ratio of a difference in an x coordinate value between a chin position of the user in the front image and a right shoulder position of the user in the front image to a difference in an x coordinate value between the chin position and a left shoulder position of the user in the front image,
the determiner determining the electrode operation patterns based on the posture parameters.

3. A posture correction method, comprising:
detecting pressures between a posture correction wear and a body of a user, by using a plurality of pressure sensors disposed at a plurality of locations on the posture correction wear, when the user wears the posture correction wear;
applying electrical muscle stimulation to the body, by using a plurality of electrical muscle stimulation electrode pairs disposed at a plurality of locations on the posture correction wear;
detecting temperatures, before and after the application of the electrical muscle stimulation, by using a plurality of temperature sensors disposed at a plurality of locations on the posture correction wear;
determining electrode operation patterns for the plurality of electrical muscle stimulation electrode pairs based on the detected pressures; and
determining whether or not to stop the application of the electrical muscle stimulation based on the temperatures.

* * * * *